US008222464B2

(12) United States Patent
Kalnes et al.

(10) Patent No.: US 8,222,464 B2
(45) Date of Patent: *Jul. 17, 2012

(54) CATALYTIC PROCESS FOR CONTINUOUSLY GENERATING POLYOLS

(75) Inventors: Tom N. Kalnes, LaGrange, IL (US); John Q. Chen, Glenview, IL (US); Joseph A. Kocal, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/193,200

(22) Filed: Jul. 28, 2011

(65) Prior Publication Data

US 2011/0313209 A1 Dec. 22, 2011

(51) Int. Cl.
C07C 29/00 (2006.01)
C07C 31/18 (2006.01)
(52) U.S. Cl. ........................................ 568/852; 568/861
(58) Field of Classification Search .................. 568/861
See application file for complete search history.

(56) References Cited

U.S. PATENT DOCUMENTS

| 4,239,633 | A | 12/1980 | Gutierrez et al. | |
|---|---|---|---|---|
| 5,227,356 | A | 7/1993 | Hess et al. | |
| 5,616,304 | A | 4/1997 | Stormo | |
| 6,162,350 | A | 12/2000 | Soled et al. | |
| 6,436,279 | B1 | 8/2002 | Colyar | |
| 6,447,645 | B1 * | 9/2002 | Barrett et al. | 162/233 |
| 6,627,780 | B2 | 9/2003 | Wu et al. | |
| 7,767,867 | B2 | 8/2010 | Cortright | |
| 7,960,594 | B2 * | 6/2011 | Zhang et al. | 568/861 |
| 2004/0175806 | A1 | 9/2004 | Werpy et al. | |
| 2009/0130502 | A1 | 5/2009 | Liu et al. | |
| 2010/0255983 | A1 * | 10/2010 | Zhang | 502/178 |
| 2011/0046419 | A1 | 2/2011 | Zhang et al. | |

FOREIGN PATENT DOCUMENTS

| WO | 2006/092085 A1 | 9/2006 |
|---|---|---|
| WO | 2010/045766 A1 | 4/2010 |
| WO | 2010/060345 A1 | 6/2010 |
| WO | 2011/113281 A1 | 9/2011 |

OTHER PUBLICATIONS

Ji et al. Catalytic conversion of cellulose into ethylene glycol over supported carbide catalysts. Catalysis Today, 2009, vol. 147, 77-85.*
Ji et al. Direct Catalytic Conversion of Cellulose into Ethylene Glycol Using Nickel-Promoted Tungsten Carbide Catalysts. Angew. Chem. Int. Ed., 2008, vol. 47, 8510-8513.*
Ji, "Catalytic conversion of cellulose into ethylene glycol over supported carbide catalysts", Catalysis Today, 2009, pp. 75-85, vol. 147, Issue 2.
Ji, "Direct Catalytic Conversion of Cellulose into Ethylene Glycol Using Nickel-Promoted Tungsten Carbide Catalysts", Angew. Chem. Int. Ed, 2008, pp. 8510-8513, vol. 47, Issue 44.
Zhang, "A new 3D mesoporous carbon replicated from commercial silica as a catalyst support for direct conversion of cellulose into ethylene glycol", Chem. Commun., 2010, pp. 862-864, vol. 46, Issue 6.
Zhang, "Hydrolysis of cellulose into glucose over carbons sulfonated at elevated temperatures", Chem Commun., 2010, pp. 6935-6937, vol. 46, Issue 37.
Zhang, "Catalytic Hydrogenation of Corn Stalk to Ethylene Glycol and 1,2-Propylene Glycol", Ind. End. Chem, Res., 2011,pp. 6601-6608, vol. 50, Issue 11.
Zhang, "Transition Metal—Tungsten Bimetallic Catalysts for the Conversion of Cellulose into Ethylene Glycol", ChemSusChem, 2010, pp. 63-66, vol. 50, Issue 11.
Jin, "Effect of Ni Promoter on Dibenzothiophene Hydrodesulfurization Performance of Molybdenum Carbide Catalyst", Chinese Jour. of Catalysis, 2006, pp. 899-903, vol. 27, Issue 10.
Narayan, "Ethylene Glycol and Other monomeric Polyols from Biomass", Biotechnology and Bioengineering Symposium, No. 14, 1984, pp. 563-571.
Zhou, "One-pot Conversion of Jerusalem Artichoke Tubers into Polyols", 7th Asia Pacific Conference on Sustainable Energy and Environmental Technologies, Oct. 15-17, 2009.
China Explores in Manufacture of Ethylene Glycol from Renewable Resources, China Petroleum processing and Petrochemical Technology, No. 1, 2009, p. 44.
Zheng, "Direct Catalytic Conversion Cellulose into Ethylene Glycol", 8th World Congress of Chemical Engineering, 2009, p. 512e.
U.S. Office action dated Dec. 9, 2011 for U.S. Appl. No. 13/192,739, Zhang et al.
U.S. Office action dated Dec. 14, 2011 for U.S. Appl. No. 13/192,835, Kalnes et al.
U.S. Office action dated Dec. 15, 2011 for U.S. Appl. No. 13/193,227, Kalnes et al.
U.S. Office action dated Dec. 9, 2011 for U.S. Appl. No. 13/192,907, Chen et al.
U.S. Office action dated Dec. 14, 2011 for U.S. Appl. No. 13/192,970, Kalnes et al.
U.S. Office action dated Dec. 15, 2011 for U.S. Appl. No. 13/193,007, Chen et al.

(Continued)

Primary Examiner — Sikarl Witherspoon
(74) Attorney, Agent, or Firm — Maryann Maas

(57) ABSTRACT

A catalytic process for generating at least one polyol from a feedstock comprising cellulose is performed in a continuous manner. The process involves, contacting, continuously, hydrogen, water, and a feedstock comprising cellulose, with a catalyst to generate an effluent stream comprising at least one polyol, water, hydrogen, and at least one co-product. The water, hydrogen, and at least one co-product are separated from the effluent stream and recycled to the reaction zone. The polyol is recovered from the effluent stream.

19 Claims, 2 Drawing Sheets

OTHER PUBLICATIONS

U.S. Office action dated Dec. 15, 2011 for U.S. Appl. No. 13/193,072, Kalnes et al.
Applicant's Mar. 9, 2012 response to the Dec. 9, 2011 Office Action for U.S. Appl. No. 13/192,739, Zhang et al.
Applicant's Mar. 14, 2012 response to the Dec. 14, 2011 Office Action for U.S. Appl. No. 13/192,835, Kalnes et al.
Applicant's Mar. 12, 2012 response to the Dec. 15, 2011 Office Action for U.S. Appl. No. 13/193,227, Kalnes et al.
Applicant's Mar. 9, 2012 response to the Dec. 9, 2011 Office Action for U.S. Appl. No. 13/192,907, Chen et al.
Applicant's Mar. 12, 2012 response to the Dec. 14, 2011 Office Action for U.S. Appl. No. 13/192,970, Kalnes et al.
Applicant's Mar. 12, 2012 response to the Dec. 15, 2011 Office Action for U.S. Appl. No. 13/193,007, Chen et al.
Applicant's Mar. 12, 2012 response to the Dec. 15, 2011 Office Action for U.S. Appl. No. 13/193,072, Kalnes et al.

* cited by examiner

CATALYTIC PROCESS FOR CONTINUOUSLY GENERATING POLYOLS

FIELD OF THE INVENTION

The invention relates to a continuous process for generating at least one polyol from a cellulose containing feedstock. The process involves, contacting, continuously, hydrogen, water, and a feedstock comprising cellulose, with a catalyst system in a reaction zone to generate an effluent stream comprising at least one polyol and recovering the polyol from the effluent stream. The effluent stream further comprises unreacted water and hydrogen and reaction intermediates which may be recycled to the reaction zone. The catalyst system comprises both a metal component with an oxidation state greater than or equal to 2+ and a hydrogenation component.

BACKGROUND OF THE INVENTION

Polyols are valuable materials with uses such as PTA/PET, cold weather fluid, cosmetics and many others. Generating polyols from cellulose instead of olefins can be a more environmentally friendly and economically attractive process. Previously, polyols have been generated from polyhydroxy compounds; see WO 2010/060345, US 2004/0175806 and WO 2006/092085. Only recently, have polyols have been catalytically generated directly from cellulose in batch type processes. Catalytic conversion of cellulose into ethylene glycol over supported carbide catalysts was disclosed in Catalysis Today, 147, (2009) 77-85. US 2010/0256424, and US 2010/0255983 teach a method of preparing ethylene glycol from cellulose and a tungsten carbide catalyst to catalyze the reaction. Tungsten carbide catalysts have also been published as successful for batch-mode direct catalytic conversion of cellulose to ethylene glycol in Angew. Chem. Int. Ed 2008, 47, 8510-8513 and supporting information. A small amount of nickel was added to a tungsten carbide catalyst in Chem. Comm. 2010, 46, 862-864. Bimetallic catalysts have been disclosed in ChemSusChem, 2010, 3, 63-66.

However, there remains a need for a catalytic process for direct conversion of cellulose to polyol that is better suited for larger scale production or ongoing production. The continuous catalytic process for generating at least one polyol from a cellulose containing feedstock described herein addresses this need.

SUMMARY OF THE INVENTION

The invention relates to a continuous process for generating at least one polyol from a cellulose containing feedstock. The process involves, contacting, in a continuous manner, hydrogen, water, and a feedstock comprising cellulose, in a reaction zone with a catalyst system to generate an effluent stream comprising at least one polyol, hydrogen, water and at least one co-product. Hydrogen, water, and the at least one co-product are separated from the effluent stream and recycled to the reaction zone. The polyol is recovered from the effluent stream. The hydrogen, water, and feedstock, are flowed in a continuous manner to the reaction zone. The effluent stream is flowed in a continuous manner from the reaction zone.

The process is a catalytic process employing a catalyst system comprising a metal component with an oxidation state greater than or equal to 2+ (M1) and a hydrogenation component (M2). The metal component M1 is selected from IUPAC Groups 4, 5 and 6 of the Periodic table, and the hydrogenation component (M2) is selected from the group consisting of IUPAC Groups 8, 9, and 10 of the Periodic Table. The metal component (M1) may be selected from the group consisting of tungsten, molybdenum, vanadium, niobium, chromium, titanium, zirconium and any combination thereof. The metal component may be comprised within a compound. The metal component is in a form other than a carbide, nitride, or phosphide The hydrogenation component may comprise, for example, an active metal component selected from the group comprising Pt, Pd, Ru, Rh, Ni, Ir, and combinations thereof. M1, M2 or both M1 and M2 may be unsupported or supported on a solid catalyst support. The solid catalyst support is selected from the group consisting of carbon, $Al_2O_3$, $ZrO_2$, $SiO_2$, MgO, $Ce_xZrO_y$, $TiO_2$, SiC, silica alumina, zeolites, clays and combinations thereof. The mass ratio of M1 to M2, on an elemental basis, ranges from about 1:100 to about 100:1. If supported, the M1 component, M2 component, or both the M1 and M2 components comprises from about 0.05 to about 30 mass percent, on an elemental basis of the supported catalyst. Measurements of the metal component and the hydrogenation component such as mass ratios, weight ratios, and mass percents are provided herein on an elemental basis with respect to the IUPAC Groups 4, 5 and 6 and IUPAC Groups 8, 9, and 10 elements of the Periodic Table.

The process may further comprise separating catalyst from the effluent stream and recycling the catalyst to the reaction zone. The catalyst may be separated from the effluent stream using a technique such as direct filtration, settling followed by filtration, hydrocyclone, fractionation, centrifugation, the use of flocculants, and precipitation. The catalyst may be reactivated prior to recycling.

In an embodiment of the invention, the polyol produced is at least ethylene glycol or propylene glycol. At least one co-product may be alcohols, organic acids, aldehydes, monosaccharides, polysaccharides, phenolic compounds, hydrocarbons, glycerol, depolymerized lignin, carbohydrates, and proteins may also be generated. In one embodiment, the feedstock may be treated prior to contacting with the catalyst system by a technique such as sizing, drying, grinding, hot water treatment, steam treatment, hydrolysis, pyrolysis, thermal treatment, chemical treatment, biological treatment, catalytic treatment, or combinations thereof.

In one embodiment, the reaction zone comprises at least a first input stream and a second input stream, the first input stream comprising at least the feedstock comprising cellulose and the second input stream comprising hydrogen. The first input stream may be pressurized prior to the reaction zone and the second input stream may be pressurized and heated prior to the reaction zone. The first input stream may be pressurized and heated to a temperature below the decomposition temperature of the cellulose prior to the reaction zone and the second input stream may be pressurized and heated prior to the reaction zone. The first input stream and the second input stream further comprise water.

The feedstock may be continuously contacted with the catalyst system in a reactor system such as an ebullating catalyst bed system, an immobilized catalyst reaction system having catalyst channels, an augured reaction system, or a slurry reactor system. When using a slurry reactor system, the temperature in the slurry reactor system may range from about 100° C. to about 350° C. and the hydrogen pressure may be greater than about 150 psig. In one embodiment, the temperature in the slurry reactor system may range from about 150° C. to about 350° C., in another embodiment the temperature in the slurry reactor system may range from about 200° C. to about 280° C. The feedstock may be continuously contacted with the catalyst system in a slurry reactor system operated at a water to feedstock comprising cellulose weight ratio ranging from about 1 to about 100, a catalyst system to feedstock comprising cellulose weight ratio of greater than about 0.005, a pH of less than about 10 and a residence time of greater than five minutes.

DETAILED DESCRIPTION OF THE INVENTION

Figure 1:
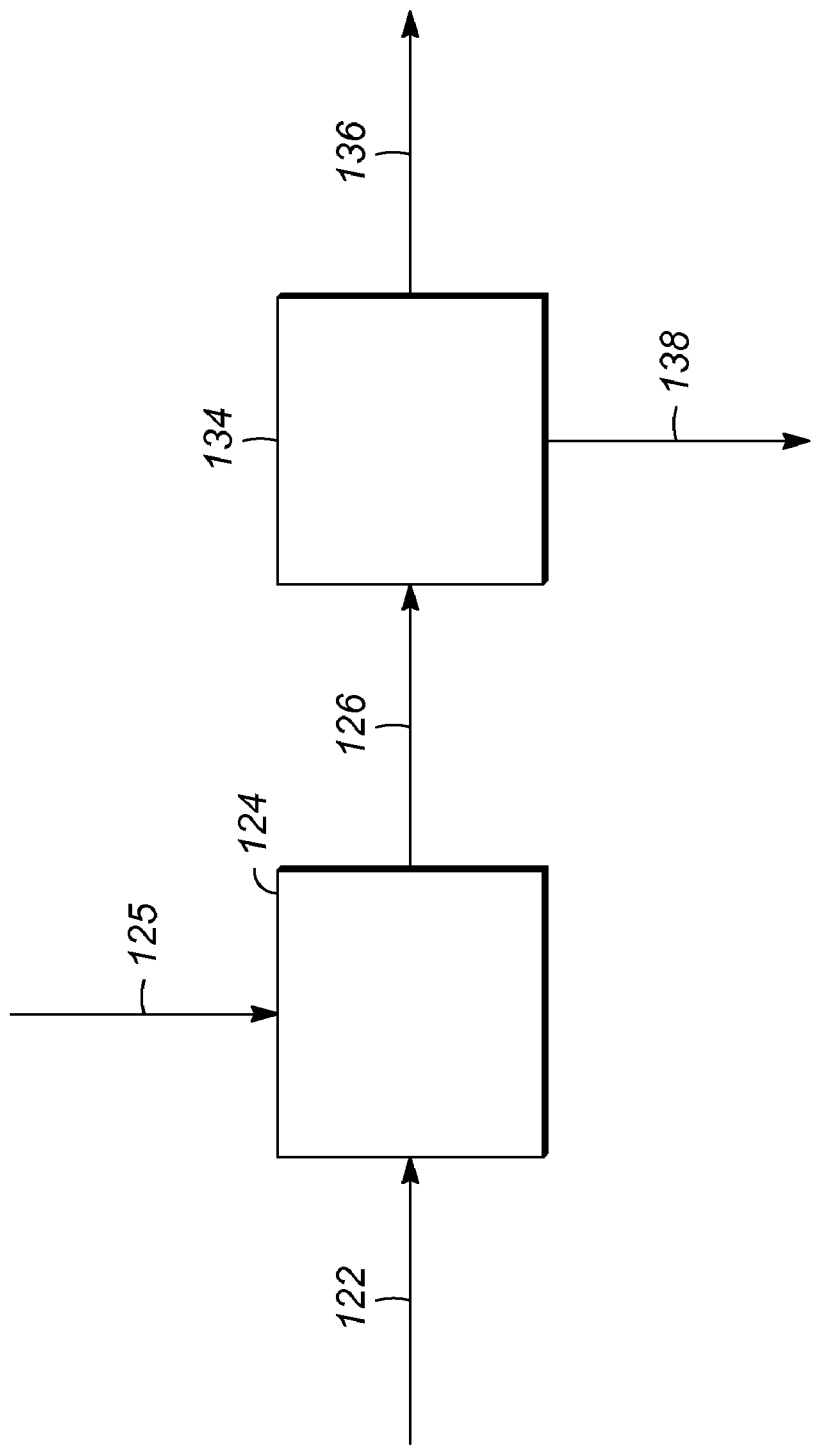
FIG. 1 is a basic diagram of the flow scheme of one embodiment of the invention. Equipment and processing steps not required to understand the invention are not depicted.

The invention involves a continuous process for generating at least one polyol from a feedstock comprising cellulose. The process involves continuous catalytic conversion of a flowing stream of cellulose to ethylene glycol or propylene glycol with high yield and high selectivity. Polyol is separated and recovered from the reaction zone effluent. Unreacted hydrogen, water, and at least one co-product are separated from the reaction zone effluent and recycled to the reaction zone. a catalyst system and a process for generating at least one polyol from a feedstock comprising at least one saccharide. The catalyst system comprises metal component (M1) with an oxidation state greater than or equal to 2+ and a hydrogenation component (M2). The metal component (M1) is selected from IUPAC Groups 4, 5 and 6 of the Periodic table. In a specific embodiment, the metal component (M1) may be selected from the group consisting of tungsten, molybdenum, vanadium, niobium, chromium, titanium, zirconium and any combination thereof. The metal component may be comprised within a compound. The metal component is not in the form of a carbide, nitride, or phosphide. The hydrogenation component (M2) is selected from the group consisting of IUPAC Groups 8, 9, and 10 of the Periodic Table. The hydrogenation component may be comprised within a compound. In a specific embodiment, the hydrogenation component may comprise an active metal component selected from the group comprising Pt, Pd, Ru, Rh, Ni, Ir, and combinations thereof. M1, M2 or both M1 and M2 may be unsupported or supported on a solid catalyst support. The solid catalyst support is selected from the group consisting of carbon, $Al_2O_3$, $ZrO_2$, $SiO_2$, MgO, $Ce_xZrO_y$, $TiO_2$, SiC, silica alumina, zeolites, clays and combinations thereof. The mass ratio of M1 to M2 ranges from about 1:100 to about 100:1 on an elemental basis. If supported, the M1 component, M2 component, or both the M1 and M2 components comprises from about 0.05 to about 30 mass percent, on an elemental basis, of the supported catalyst. Measurements of the metal component and the hydrogenation component such as mass ratios, weight ratios, and mass percents are provided herein on an elemental basis with respect to the IUPAC Groups 4, 5 and 6 and IUPAC Groups 8, 9, and 10 elements of the Periodic Table.

In one embodiment, the feedstock to the process comprises at least cellulose. Economic conversion of cellulose to useful products can be a sustainable process that reduces fossil energy consumption and does not directly compete with the human food supply. Cellulose is a large renewable resource having a variety of attractive sources, such as residue from agricultural production or waste from forestry or forest products. Since cellulose cannot be digested by humans, using cellulose as a feedstock does not take from our food supply. Furthermore, cellulose can be a low cost waste type feedstock material which is converted herein to high value products like polyols such as ethylene glycol and propylene glycol. In another embodiment, the feedstock to the process comprises at least hemicellulose.

The cellulose containing feedstock may be derived from sources such as biomass, pulp derived from biomass, waste material, and recycled material. Examples include short rotation forestry, industrial wood waste, forest residue, agricultural residue, energy crops, industrial wastewater, municipal wastewater, paper, cardboard, fabrics and combinations thereof. Multiple materials may be used as co-feedstocks. With respect to biomass, the feedstock may be whole biomass including lignin and hemicellulose, treated biomass where the cellulose is at least partially depolymerized, or where the ligin, hemicellulose, or both have been at least partially removed from the whole biomass.

Unlike batch system operations, in a continuous process, the feedstock is continually being introduced into the reaction zone as a flowing stream and a product comprising a polyol is being continuously withdrawn. Materials must be capable of being transported from a source into the reaction zone, and products must be capable of being transported from the reaction zone. Depending upon the mode of operation, residual solids, if any, may be capable of being removed from the reaction zone.

A challenge in processing a cellulose containing feedstock in a pressurized hydrogen environment is that the feedstock is typically a solid. Therefore, pretreatment of the feedstock may be performed in order to facilitate the continuous transporting of the feedstock. Suitable pretreatment operations may include sizing, drying, grinding, hot water treatment, steam treatment, hydrolysis, pyrolysis, thermal treatment, chemical treatment, biological treatment, catalytic treatment, and combinations thereof. Sizing, grinding or drying may result in solid particles of a size that may be flowed or moved through a continuous process using a liquid or gas flow, or mechanical means. An example of a chemical treatment is mild acid hydrolysis, an example of catalytic treatment is catalytic hydrolysis, catalytic hydrogenation, or both, and an example of biological treatment is enzymatic hydrolysis. Hot water treatment, steam treatment, thermal treatment, chemical treatment, biological treatment, or catalytic treatment may result in lower molecular weight saccharides and depolymerized lignins that are more easily transported as compared to the untreated cellulose. Suitable pretreatment techniques are found in Ind. Eng. Chem. Res._DOI:10.1021/ie102505y, Publication Date (Web): Apr. 20, 2011 "Catalytic Hydrogenation of Corn Stalk to Ethylene Glycol and 1,2-Propylene Glycol" Jifeng Pang, Mingyuan Zheng, Aiqin Wang, and Tao Zhang. See also, US 2002/0059991.

Another challenge in processing a cellulose containing feedstock is that the cellulose is thermally sensitive. Exposure to excessive heating prior to contacting with the catalyst system may result in undesired thermal reactions of the cellulose such as charring of the cellulose. In one embodiment of the invention, the feedstock comprising cellulose is provided to the reaction zone containing the catalyst system in a separate input stream from the primary hydrogen stream. In this embodiment, the reaction zone has at least two input streams. The first input stream comprises at least the feedstock comprising cellulose, and the second input stream comprises at least hydrogen. Water may be present in the first input stream, the second input stream or in both input streams. Some hydrogen may also be present in the first input stream with the feedstock comprising cellulose. By separating the feedstock comprising cellulose and the hydrogen into two independent input streams, the hydrogen stream may be heated in excess of the reaction temperature without also heating the feedstock comprising cellulose to reaction temperature or above. The temperature of first input stream comprising at least the feedstock comprising cellulose may be controlled not to exceed the temperature of unwanted thermal side reactions. For example, the temperature of first input stream comprising at least the feedstock comprising cellulose may be controlled not to exceed the decomposition temperature of the cellulose or the charring temperature of the cellulose. The first input stream, the second input stream, or both may be pressurized to reaction pressure before being introduced to the reaction zone.

The feedstock comprising cellulose, after any pretreatment, is continuously introduced to a catalytic reaction zone as a flowing stream. Water and hydrogen, both reactants, are introduced to the reaction zone. As discussed above and depending upon the specific embodiment, at least a portion of the hydrogen may be introduced separately and independent from the feedstock comprising cellulose, or any combination of reactants, including feedstock comprising cellulose, may be combined and introduced to the reaction zone together. Because of the mixed phases likely to be present in the reaction zone specific types of systems are preferred. For example, suitable systems include ebullating catalyst bed systems, immobilized catalyst reaction systems having catalyst channels, augured reaction systems, fluidized bed reactor systems, mechanically mixed reaction systems or slurry reactor systems, also known as a three phase bubble column reactor systems.

Furthermore, metallurgy of the reaction zone is selected to be compatible with the reactants and the desired products within the range of operating conditions. Examples of suitable metallurgy for the reaction zone include titanium, zirconium, stainless steel, carbon steel having hydrogen embrittlement resistant coating, carbon steel having corrosion resistant coating. In one embodiment, the metallurgy of the reaction zone includes zirconium clad carbon steel.

Within the reaction zone and at operating conditions, the reactants proceed through catalytic conversion reactions to produce at least one polyol. Desired polyols include ethylene glycol and propylene glycol. At least one co-products is also be produced and may be a compound such as alcohols, organic acids, aldehydes, monosaccharides, polysaccharides, phenolic compounds, hydrocarbons, glycerol, depolymerized lignin, carbohydrates, and proteins. More than one co-product may be produced. Some of the co-products may have value and may be recovered in addition to the product polyols. Co-products may also be reaction intermediates which may be separated from the reaction zone effluent and recycled to the reaction zone. Unreacted hydrogen, water, and cellulose may also be present in the reaction zone effluent along with co-products. Unreacted hydrogen, water, and cellulose may be separated and recycled to the reaction zone. The reaction zone of the process may be operated at conditions sufficient to maintain at least a portion of the water in the reaction mixture in the liquid phase.

The reactions are catalytic reactions and the reaction zone comprises at least one catalyst system where the catalyst system comprises a metal component with an oxidation state greater than or equal to 2+ (M1) and a hydrogenation component (M2). The metal component M1 is selected from IUPAC Groups 4, 5 and 6 of the Periodic table, and the hydrogenation component (M2) is selected from the group consisting of IUPAC Groups 8, 9, and 10 of the Periodic Table. The catalyst system may also be considered a multi-component catalyst, and the terms are used herein interchangeably.

The metal component (M1) may be present in the catalyst system in any catalytically available form that has the metal component in an oxidation state greater than or equal to 2+. The metal component may be in a compound or may be in chemical combination with one or more of the other ingredients of the catalyst system. For example, the metal component (M1) may be selected from the group consisting of tungsten, molybdenum, vanadium, niobium, chromium, titanium, zirconium and any combination thereof. The metal component may be comprised within a compound. The metal component is in a form other than a carbide, nitride, or phosphide. Compounds comprising the M1 component of the catalyst system may be selected from the group consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. The hydrogenation component (M2) may be present in the catalyst system in any catalytically available form. The hydrogenation component may in the elemental form or may be a compound or may be in chemical combination with one or more of the other ingredients of the catalyst system. For example, the hydrogenation component may comprise an active metal component selected from the group comprising Pt, Pd, Ru, Rh, Ni, Ir, and combinations thereof.

The metal component M1, the hydrogenation component M2 or both M1 and M2 may be unsupported or supported on one or more solid catalyst supports. Refractory oxide catalyst supports and others may be used. The mass ratio of M1 to M2, on an elemental basis, ranges from about 1:100 to about 100:1. If supported, the M1 component, M2 component, or both the M1 and M2 components comprises from about 0.05 to about 30 mass percent, on an elemental basis, of the supported catalyst. The description below generally refers to the catalyst support. Such general description to the catalyst support is not meant to limit the broad scope of the invention to a single catalyst support. For example in one embodiment M1 is supported on a first catalyst support and M2 is supported on a second catalyst support and the first catalyst support and the second catalyst support may be the same composition or different compositions.

The support may be in the shape of a powder, or specific shapes such as spheres, extrudates, pills, pellets, tablets, irregularly shaped particles, monolithic structures, catalytically coated tubes, or catalytically coated heat exchanger surfaces. Examples of the refractory inorganic oxide supports include but are not limited to silica, aluminas, silica-alumina, titania, zirconia, magnesia, clays, zeolites, molecular sieves, etc. It should be pointed out that silica-alumina is not a mixture of silica and alumina but means an acidic and amorphous material that has been cogelled or coprecipitated. Carbon and activated carbon may also be employed as supports. Specific suitable supports include carbon, activated carbon, $Al_2O_3$, $ZrO_2$, $SiO_2$, MgO, $Ce_xZrO_y$, $TiO_2$, SiC, silica alumina, zeolites, clays and combinations thereof. Of course, combinations of materials can be used as the support. M1, M2, or the combination of M1 and M2 may be incorporated onto the catalytic support in any suitable manner known in the art, such as by coprecipitation, coextrusion with the support, or impregnation. M1, M2, or the combination of M1 and M2 may comprise from about 0.05 to about 30 mass %, on an elemental basis, of the supported catalyst. In another embodiment, M1, M2, or the combination of M1 and M2 may comprise from about 0.3 to about 15 mass %, on an elemental basis, of the supported catalyst. In still another embodiment, M1, M2, or the combination of M1 and M2 may comprise from about 0.5 to about 7 mass %, on an elemental basis, of the supported catalyst.

The relative amount of M1 catalyst component to M2 catalyst component may range from about 1:100 to about 100:1 as measured by ICP or other common wet chemical analysis methods, on an elemental basis. In another embodiment, the relative amount of M1 catalyst component to M2 catalyst component may range from about 1:20 to about 50:1, on an elemental basis, and in still another embodiment, the relative amount of M1 catalyst component to M2 catalyst component may range from about 1:10 to about 10:1, on an elemental basis.

The amount of the catalyst system used in the process may range from about 0.005 to about 0.4 mass % of the feedstock comprising saccharide, with the catalyst system measured on an elemental basis. In other embodiment, the amount of the catalyst system used in the process may range from about 0.01 to about 0.25 mass % of the feedstock comprising saccharide, with the catalyst system measured on an elemental basis. In still other embodiments, the amount of the catalyst system used in the process may range from about 0.02 to about 0.15 mass % of the feedstock comprising saccharide, with the catalyst system measured on an elemental basis. The reactions occurring are multistep reactions and different amounts of the catalyst system, or relative amounts of the components of the catalyst system, can be used to control the rates of the different reactions. Individual applications may have differing requirements as to the amounts of the catalyst system, or relative amounts of the components of the catalyst system used.

In one embodiment of the invention, the M1 catalyst component may be a solid that is soluble in the reaction mixture, or at least partially soluble in the reaction mixture which includes at least water and the feedstock at reaction conditions. An effective amount of the solid M1 catalyst should be soluble in the reaction mixture. Different applications and M1 catalyst components will result in differing effective amounts of M1 catalyst component needed to be in solution in the reaction mixture. In another embodiment of the invention, the M1 catalyst component is miscible or at least partially miscible with the reaction mixture. As with the solid M1 catalyst component, an effective amount of the liquid M1 catalyst should be miscible in the reaction mixture. Again, different applications and different M1 catalyst components will result in differing effective amounts of M1 catalyst component needed to be miscible in the reaction mixture. Typically, the amount of M1 catalyst component miscible in water is in the range of about 1 to about 100%, in another embodiment, from about 10 to about 100%, and in still another embodiment, from about 20 to about 100%.

The multicomponent catalyst of the present invention may provide several advantages over a more traditional single component catalyst. For example, in some embodiments, the manufacture costs of the catalyst may be reduced since fewer active components need to be incorporated onto a solid catalyst support. Operational costs may be reduced since it is envisioned that less catalyst make-up will be required and more selective processing steps can be used for recovery and recycle of catalyst. Other advantages include improved catalyst stability which leads to lower catalyst consumption and lower cost per unit of polyol product, and the potential for improved selectivity to ethylene glycol and propylene glycol with reduced production of co-boiling impurities such as butane diols.

In some embodiments all or a portion of the catalyst system may reside within the reaction zone, and in other embodiments the catalyst may continuously or intermittently pass through the reaction zone. Suitable systems include ebullating catalyst bed systems, immobilized catalyst reaction systems having catalyst channels, augured reaction systems, fluidized bed reactor systems, mechanically mixed reaction systems and slurry reactor systems, also known as a three phase bubble column reactor systems.

In one embodiment of the invention, the catalytic reaction zone employs a slurry reactor. Slurry reactor systems are known in the art and an example of a slurry reactor system is described in U.S. Pat. No. 5,616,304 and in Topical Report, Slurry Reactor Design Studies, DOE Project No. DE-AC22-89PC89867, Reactor Cost Comparisons.

The catalyst system may be mixed with the feedstock comprising cellulose and water to form a slurry which is conducted to the slurry reactor. The reactions occur within the slurry reactor and the catalyst is transported with the effluent stream out of the reactor. The slurry reactor system may be operated at temperatures from about 100° C. to about 350° C. and the hydrogen pressure may be greater than about 150 psig. In one embodiment, the temperature in the slurry reactor system may range from about 150° C. to about 350° C., in another embodiment the temperature in the slurry reactor system may range from about 200° C. to about 280° C. The feedstock may be continuously contacted with the catalyst system in a slurry reactor system operated at a water to feedstock comprising cellulose weight ratio ranging from about 1 to about 100, a catalyst to feedstock comprising cellulose weight ratio of greater than about 0.005, a pH of less than about 10 and a residence time of greater than 5 minutes. In another embodiment, the water to feedstock comprising cellulose weight ratio ranges from about 1 to about 20 and the catalyst system to feedstock comprising cellulose weight ratio is greater than about 0.01 with the catalyst system measured on an elemental basis. In yet another embodiment, the water to feedstock comprising cellulose weight ratio ranges from about 1 to about 5 and the catalyst to feedstock comprising cellulose weight ratio is greater than about 0.1 with the catalyst system measured on an elemental basis.

In another embodiment the catalytic reaction zone employs an ebullating bed reactor. Ebullating bed reactor systems are known in the art and an example of an ebullating bed reactor system is described in U.S. Pat. No. 6,436,279.

The effluent stream from the reaction zone contains at least the product polyol(s) and unreacted water, hydrogen, and at least one co-product such as alcohols, organic acids, aldehydes, monosaccharides, polysaccharides, phenolic compounds, hydrocarbons, glycerol, depolymerized lignin, carbohydrates, and proteins. Unreacted cellulose may also be present in the reaction zone effluent stream. At least the water, hydrogen, and one co-product are separated from the reaction zone effluent stream and recycled to the reaction zone. Unreacted cellulose may also be separated from the reaction zone effluent stream and recycled to the reaction zone.

In one embodiment, the hydrogen is separated from the effluent stream before the water is separated from the effluent stream. The separated hydrogen may be recycled to one or more of a number of different locations within the process depending upon the specific embodiment employed. For example, the separated hydrogen maybe recycled to a reactor in the reaction zone. The recycled hydrogen may be combined with fresh hydrogen or make-up hydrogen before being introduced into a reactor of the reaction zone, or recycled hydrogen may be introduced to a reactor in the reaction zone independently of fresh hydrogen or make-up hydrogen. The separated hydrogen may be pressurized to the pressure of the reaction zone, and heated to or above the temperature of the reaction zone. The separated hydrogen may be purified before recycling. A gas-liquid separator may be used to separate the hydrogen from the effluent stream.

Similarly, the water may be recycled to one or more of a number of different locations within the process depending upon the specific embodiment employed. For example, the separated water may be recycled to combine with the feedstock comprising cellulose or pretreated feedstock comprising cellulose. The separated water may be added to an optional pretreatment operation, or may be added to the reaction zone. The water may be purified before being recycled.

Furthermore, the reaction zone may comprise a mixing zone upstream of a reactor. When a mixing zone is employed, the separated hydrogen may be recycled to the reactor while the separated water may be recycled to the mixing zone.

In a product recovery zone, at least the polyols are separated from the effluent stream. In one embodiment, the co-products are also separated from the effluent stream in the product recovery zone. Multiple separated stream may be produced by the product recovery zone; ethylene glycol may be separated into an ethylene glycol stream, propylene glycol maybe separated into a propylene glycol stream, co-products having a molecular weight lower than ethylene glycol, such as alcohols, may be separated into a low molecular weight co-product stream, co-products having a molecular weight higher than propylene glycol, such as glycerol, may be separated into a high molecular weight co-product stream, fuel gas may be separated into a fuel gas stream, and non-volatile residues may be separated into a non-volatile residue stream. Additional co-product streams may be separated so that classes or individual co-products are separated. One or more of the co-products streams may be recycled to the reaction zone. In the embodiment where the reaction zone comprises a mixing zone upstream of a reactor, the separated at least one co-product may be recycled to the reactor, the mixing zone, or both. Depending upon the catalyst selected and the catalytic reaction system used, the product recovery zone may also separate catalyst from the effluent stream. The product polyol stream(s) may be purified in a product purification zone to generate high purity polyol.

Depending on the catalytic reaction system used, the effluent stream may also contain solid catalyst particles. In some embodiments it may be advantageous to remove the solid catalyst particles from the effluent stream, either before or after and desired products or co-products are recovered. Catalyst particles may be removed from the effluent stream using one or more techniques such as direct filtration, settling followed by filtration, hydrocyclone, fractionation, centrifugation, the use of flocculants, precipitation, extraction, evaporation, or combinations thereof. In one embodiment, the catalyst particles are separated from the effluent stream after the hydrogen is separated from the effluent stream and before the water is separated from the effluent stream. In another embodiment, separated catalyst particles may be recycled to the reaction zone. In yet another embodiment, the separated catalyst particles may be reactivated before being recycled to the reaction zone. In the embodiment where the reaction zone comprises a mixing zone upstream of a reactor, the separated at least one co-product may be recycled to the reactor, the mixing zone, or both.

Turning to FIG. 1, catalyst, water, and feedstock comprising cellulose is conducted via stream 122 to reaction zone 124. The mixture in stream 122 has, for example, a water to feedstock comprising cellulose weight ratio of about 5 and a catalyst to feedstock comprising cellulose weight ratio of about 0.05. At least hydrogen is conducted via stream 125 to reaction zone 124. Reaction zone 124 is operated at, for example, a temperature of about 250° C. a hydrogen pressure of about 1200 psig, a pH of about 7 and a residence time of about 8 minutes. Prior to introduction into reaction zone 124, the catalyst, water, and feedstock comprising cellulose in stream 122 and the hydrogen in stream 125 are brought to a pressure of about 1800 psig to be at about the same pressure as reaction zone 124. However, only stream 125 comprising at least hydrogen, while upstream of zone 124, is raised to at least 250° C. to be at about the temperature of reaction zone 124. The mixture in stream 122 which contains at least the cellulose is temperature controlled to remain at a temperature lower than the decomposition or charring temperature of the cellulose. In reaction zone 124, the cellulose is catalytically converted into at least ethylene glycol or polyethylene glycol. Reaction zone effluent 126 contains at least the product ethylene glycol or propylene glycol, hydrogen, water, and at least one co-product such as alcohols, organic acids, aldehydes, monosaccharides, polysaccharides, phenolic compounds, hydrocarbons, glycerol, depolymerized lignin, carbohydrates, and proteins. Hydrogen is separated from reaction zone effluent in line 115 and recycled to reaction zone 124. The separated hydrogen in line 115 may be combined with hydrogen stream 125 as shown. Water is separated from reaction zone effluent in line 118 and recycled to reaction zone 124. The remaining portion of reaction zone effluent 126 is conducted to product recovery zone 134 where the desired glycol products are separated and recovered in steam 136. At least one co-product is separated into co-product stream 116 and recycled to reaction zone 124. Remaining components of reaction zone effluent 126 are removed from product recovery zone 134 in stream 138.

Figure 2:
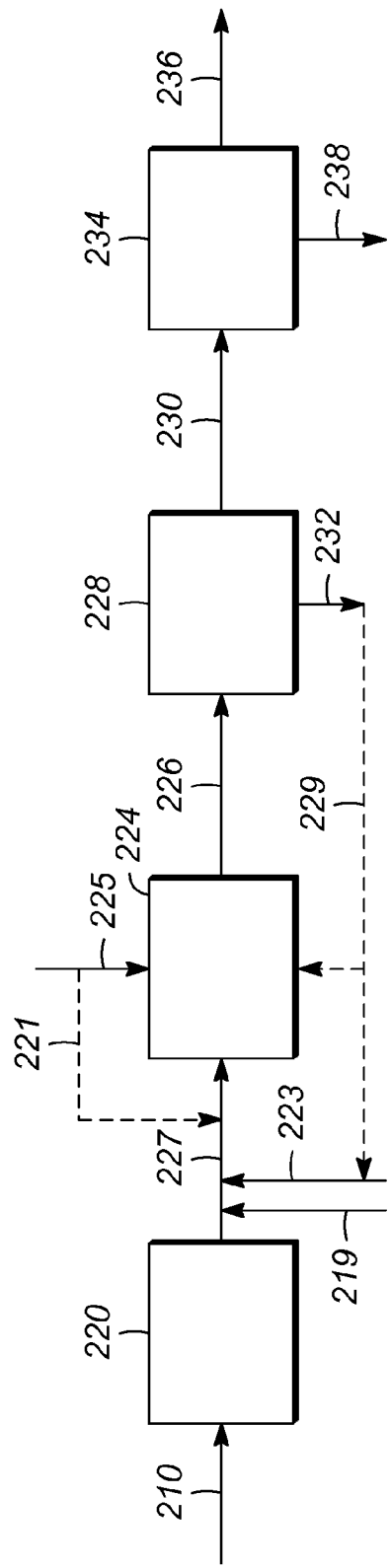
FIG. 2 is a basic diagram of the flow scheme of another embodiment of the invention. Equipment and processing steps not required to understand the invention are not depicted.

Turning to FIG. 2, water and feedstock comprising cellulose 210 is introduced to pretreatment unit 220 where the cellulose is ground to a particle size that is small enough to be pumped as a slurry with the water using conventional equipment and removed from pretreatment unit 220 in line 219. Reaction zone 224 contains mixing zone 224*a* and reactor 224*b*. The pretreated feedstock in line 219 is conducted to mixing zone 224*a* of reaction zone 224 and combined with water from line 221 and catalyst from line 223. Mixed stream 213 from mixing zone 213 has, for example, a water to feedstock comprising cellulose weight ratio of about 5 and a catalyst to feedstock comprising cellulose weight ratio of about 0.05. At least hydrogen is conducted via stream 225 to reactor 224*b* of reaction zone 224. Some hydrogen may be combined with stream 213 or stream 219 prior to reactor 224*b* (not shown). Reactor 224*b* is operated at, for example, a temperature of about 250° C. a hydrogen pressure of about 1200 psig, a pH of about 7 and a residence time of about 8 minutes. Prior to introduction into reactor 224*b*, the catalyst, water, and pretreated feedstock comprising cellulose in stream 213 and the hydrogen in stream 225 are brought to a pressure of about 1800 psig to be at about the same temperature as reactor 224*b*. However, only stream 225 comprising at least hydrogen, while upstream of reactor 224*b*, is raised to, for example, at least 250° C. to be at about the temperature of reactor 224*b*. The mixture in stream 213 which contains at least the cellulose is temperature controlled to remain at a temperature lower than the decomposition or charring temperature of the cellulose. In reactor 224b, the cellulose is catalytically converted into at least ethylene glycol or polyethylene glycol.

Reactor effluent 226 contains at least the product ethylene glycol or propylene glycol, hydrogen, water, at least one co-product and catalyst. The at least one co-product may be alcohols, organic acids, aldehydes, monosaccharides, polysaccharides, phenolic compounds, hydrocarbons, glycerol, depolymerized lignin, carbohydrates, and proteins. Reactor effluent 226 is conducted to hydrogen separation zone 240 where at least a portion of the hydrogen is removed in line 215 and recycled to reactor 224b through combining with hydrogen stream 225 (shown) or directly to reactor 224b (not shown). The hydrogen depleted reactor effluent in line 242 is conducted to water separation zone 244 where at least a portion of the water is separated into line 218 and recycled to mixing zone 224a by combining with water stream 221 (shown) or directly to mixing zone 224a (not shown).

Hydrogen and water depleted reactor effluent in line 246 is conducted to optional catalyst recovery zone 228 where the catalyst is separated and removed in line 232. Catalyst in line 232 may optionally be recycled to combine with line 223 (shown) or directly to mixing zone 224a (not shown). The catalyst-depleted reactor effluent 230 is conducted to product recovery zone 234 where the desired glycol products are separated and recovered in steam 236. At least one co-product is separated into line 216 and recycled to mixing zone 224a. Remaining components of catalyst-depleted reactor effluent 230 are removed from product recovery zone 234 in stream 238.

EXAMPLE

Seventeen experiments were conducted according to the following procedure. 1 gram of saccharide containing feedstock and 100 grams of de-ionized water were added to a 300 ml Parr autoclave reactor. An effective amount of catalyst containing M1 and M3 components were added to the reactor. Details of the feedstocks and type and amount of catalyst are shown in the Table. The autoclave was sealed and purged with $N_2$ followed by $H_2$ and finally pressurized with $H_2$ to about 6 MPa at room temperature. The autoclave was heated up to 245° C. with constant stirring at about 1000 rpm and kept at temperature for 30 minutes. After 30 minutes, the autoclave was cooled down to room temperature and liquid product was recovered by filtration and analyzed using HPLC. Microcrystalline cellulose was obtained from Sigma-Aldrich. Ni on Norit CA-1 catalyst was prepared by impregnating various amounts of Ni using Ni nitrate in water onto activated carbon support Norit-CA1 using incipient wetness technique. The impregnated support was then dried at 40° C. overnight in an oven with nitrogen purge and reduced in H2 at 750° C. for 1 hrs. 5% Pd/C and 5% Pt/C were purchased from Johnson Matthey. Ethylene glycol and propylene glycol yields were measured as mass of ethylene glycol or propylene glycol produced divided by the mass of feedstock used and multiplied by 100.

| No. | Feedstock Type | Feedstock Amount (g) | H2O (g) | Unsupported Catalyst Component (M1) | M1 in Reactor (g) | Supported Catalyst Component (M2) | M2 in Reactor (g) | M1/M2 (wt/wt) | (M1 + M2)/ Feedstock (wt/wt) | EG Yield (wt %) | PG Yield (wt %) |
|---|---|---|---|---|---|---|---|---|---|---|---|
| 1 | Microcrystalline Cellulose | 1 | 100 | None | 0 | 2% Ni/Norit CA-1 | 0.006 | 0.0 | 0.006 | 2.3 | 1.9 |
| 2 | Microcrystalline Cellulose | 1 | 100 | Tungstic Acid, $WO_3 \cdot xH_2O$ | 0.015 | 2% Ni/Norit CA-1 | 0.006 | 2.5 | 0.021 | 58.0 | 4.3 |
| 3 | Microcrystalline Cellulose | 1 | 100 | Tungsten Oxide, $WO_2$ | 0.008 | 0.6% Ni/Norit CA-1 | 0.0018 | 4.4 | 0.010 | 55.0 | 4.1 |
| 4 | Microcrystalline Cellulose | 1 | 100 | Phosphotungstic Acid $H_3PW_{12}O_{40}$ | 0.015 | 2% Ni/Norit CA-1 | 0.006 | 2.5 | 0.021 | 46.0 | 4.6 |
| 5 | Microcrystalline Cellulose | 1 | 100 | Ammonium Metatungstate $(NH_4)_6(W_{12}O_{40}) \cdot xH_2O$ | 0.015 | 2% Ni/Norit CA-1 | 0.006 | 2.5 | 0.021 | 56.0 | 3.0 |
| 6 | Microcrystalline Cellulose | 1 | 100 | Ammonium Metatungstate $(NH_4)_6(W_{12}O_{40}) \cdot xH_2O$ | 0.03 | 2% Ni/Norit CA-1 | 0.006 | 5.0 | 0.036 | 55.0 | 3.0 |
| 7 | Microcrystalline Cellulose | 1 | 100 | Ammonium Metatungstate $(NH_4)_6(W_{12}O_{40}) \cdot xH_2O$ | 0.06 | 2% Ni/Norit CA-1 | 0.006 | 10.0 | 0.066 | 49.0 | 2.0 |
| 8 | Microcrystalline Cellulose | 1 | 100 | Ammonium Metatungstate $(NH_4)_6(W_{12}O_{40}) \cdot xH_2O$ | 0.12 | 2% Ni/Norit CA-1 | 0.006 | 20.0 | 0.126 | 37.0 | 1.7 |
| 9 | Microcrystalline Cellulose | 1 | 100 | Ammonium Metatungstate $(NH_4)_6(W_{12}O_{40}) \cdot xH_2O$ | 0.015 | 1% Ni/Norit CA-1 | 0.003 | 5.0 | 0.018 | 68.0 | 2.8 |
| 10 | Microcrystalline Cellulose | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 68.0 | 3.3 |
| 11 | Microcrystalline Cellulose | 1 | 100 | Ammonium Metatungstate $(NH_4)_6(W_{12}O_{40}) \cdot xH_2O$ | 0.008 | 0.2% Ni/CA-1 | 0.0006 | 13.3 | 0.009 | 38.0 | 0.0 |
| 12 | Microcrystalline Cellulose | 1 | 100 | Ammonium Metatungstate $(NH_4)_6(W_{12}O_{40}) \cdot xH_2O$ | 0.06 | 5% Pd/C | 0.015 | 4.0 | 0.075 | 48.0 | 0.0 |
| 13 | Microcrystalline Cellulose | 1 | 100 | Ammonium Metatungstate $(NH_4)_6(W_{12}O_{40}) \cdot xH_2O$ | 0.015 | 5% Pd/C | 0.015 | 1.0 | 0.030 | 42.0 | 1.0 |

-continued

| No. | Feedstock Type | Feedstock Amount (g) | H2O (g) | Unsupported Catalyst Component (M1) | M1 in Reactor (g) | Supported Catalyst Component (M2) | M2 in Reactor (g) | M1/M2 (wt/wt) | (M1 + M2)/ Feedstock (wt/wt) | EG Yield (wt %) | PG Yield (wt %) |
|---|---|---|---|---|---|---|---|---|---|---|---|
| 14 | Microcrystalline Cellulose | 1 | 100 | Ammonium Metatungstate $(NH_4)_6(W_{12}O_{40}) \cdot xH_2O$ | 0.015 | 5% Pt/C | 0.015 | 1.0 | 0.030 | 17.2 | 2.4 |
| 15 | Bleached Pulp | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 37.0 | 3.0 |
| 16 | Glucose | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 29.0 | 6.6 |
| 17 | Glucose | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 49.0 | 4.1 |

The invention claimed is:

1. A process for generating at least one polyol from a feedstock comprising cellulose, the process comprising:
    a) contacting, in a continuous manner, in a reaction zone, hydrogen, water, and a feedstock comprising cellulose, with a catalyst system comprising an unsupported component comprising a compound comprising an element selected from the group consisting of IUPAC Groups 4, 5 and 6 of the Periodic Table and having an oxidation state greater than or equal to 2+ wherein the compound of the unsupported component is in a form other than a carbide, nitride or phosphide, and a supported hydrogenation component comprising an element selected from the group consisting of IUPAC Groups 8, 9, and 10, of the Periodic Table on a solid catalyst support;
    b) separating hydrogen from the effluent stream and recycling at least a portion of the separated hydrogen to the reaction zone;
    c) separating water from the effluent stream and recycling at least a portion of the separated water to the reaction zone; and
    d) recovering the polyol from the effluent stream.

2. The process of claim 1 further comprising separating at least one co-product from the effluent stream and recycling at least a portion of the separated co-product to the reaction zone.

3. The process of claim 1 wherein the effluent stream further comprises cellulose and the process further comprises separating the cellulose from the effluent stream and recycling at least a portion of the separated cellulose to the reaction zone.

4. The process of claim 1 wherein the effluent stream further comprises at least a portion of the catalyst system, said process further comprising separating at least a portion of the catalyst from the effluent stream and recycling separated catalyst to the reaction zone.

5. The process of claim 4 further comprising reactivating the separated catalyst prior to recycling the catalyst to the reaction zone.

6. The process of claim 4 wherein the catalyst system is separated from the effluent stream using a technique selected from the group consisting of direct filtration, settling followed by filtration, hydrocyclone, fractionation, centrifugation, the use of flocculants, precipitation, liquid extraction, evaporation, and combinations thereof.

7. The process of claim 4 wherein at least a portion of the catalyst system is separated from the effluent stream after the hydrogen is separated from the effluent stream, and before the water is separated from the effluent stream.

8. The process of claim 1 wherein the reaction zone comprises a mixing zone upstream of a reactor and wherein the separated hydrogen is recycled to the reactor and the separated water is recycled to the mixing zone.

9. The process of claim 2 wherein the reaction zone comprises a mixing zone upstream of a reactor and wherein at least a portion of the separated at least one co-product is recycled to the reactor, the mixing zone, or both.

10. The process of claim 1 wherein the hydrogen is separated from the effluent stream before the water is separated from the effluent stream.

11. The process of claim 2 wherein the at least one co-product is separated after the hydrogen and the water are separated from the effluent stream.

12. The process of claim 2 wherein the at least one co-product is selected from the group consisting of alcohols, organic acids, aldehydes, monosaccharides, polysaccharides, phenolic compounds, hydrocarbons, glycerol, depolymerized lignin, carbohydrates, and proteins.

13. The process of claim 1 wherein the reaction zone comprises at least a first input stream and a second input stream, the first input stream comprising at least the feedstock comprising cellulose and the second input stream comprising hydrogen.

14. The process of claim 13 wherein the first input stream is pressurized prior to the reaction zone and the second input stream is pressurized and heated prior to the reaction zone.

15. The process of claim 13 wherein the first input stream is pressurized and heated to a temperature below the decomposition temperature of the cellulose prior to the reaction zone and the second input stream is pressurized and heated prior to the reaction zone.

16. The process of claim 13 wherein the first input stream and the second input stream further comprise water.

17. The process of claim 1 wherein the feedstock comprising cellulose is selected from the group consisting of biomass, pulp derived from biomass, waste material, recycled material, short rotation forestry, industrial wood waste, forest residue, agricultural residue, energy crops, industrial wastewater, municipal wastewater, paper, cardboard, fabrics and combinations thereof.

18. The process of claim 1 further comprising preparing the feedstock comprising cellulose prior to contacting with the catalyst by a technique selected from the group consisting of sizing, drying, grinding, hot water treatment, steam treatment, hydrolysis, pyrolysis, thermal treatment, chemical treatment, biological treatment, catalytic treatment, and combinations thereof.

19. The process of claim 1 wherein the reaction zone comprises a system selected from the group consisting of an ebullating catalyst bed reaction system, an immobilized catalyst reaction system having catalyst channels, an augured reaction system, a fluidized bed reaction system, a mechanically mixed reaction system, and a slurry reactor system.

* * * * *